United States Patent [19]
Noda

[11] Patent Number: 5,366,476
[45] Date of Patent: Nov. 22, 1994

[54] HANDLE FOR LAPAROSCOPIC INSTRUMENT

[75] Inventor: Wayne A. Noda, Mission Viejo, Calif.

[73] Assignee: Laparomed Corporation, Irvine, Calif.

[21] Appl. No.: 42,329

[22] Filed: Apr. 2, 1993

[51] Int. Cl.⁵ ............................................. A61B 10/00
[52] U.S. Cl. .................................. 606/206; 606/41; 606/45; 606/46; 606/48
[58] Field of Search ............... 606/41, 42, 45–52, 606/205–209

[56] References Cited

U.S. PATENT DOCUMENTS

| | | | |
|---|---|---|---|
| 4,418,692 | 12/1983 | Guay | 606/51 |
| 4,672,964 | 6/1987 | Dee et al. | |
| 4,700,702 | 10/1987 | Nilsson | |
| 4,760,848 | 8/1988 | Hasson | 606/206 |
| 4,784,137 | 11/1988 | Kulik et al. | |
| 4,976,269 | 12/1990 | Mehl | 128/754 |
| 4,991,600 | 2/1991 | Taylor | 128/754 |
| 5,133,735 | 7/1992 | Slater et al | 606/205 |
| 5,141,517 | 8/1992 | Shutt | 606/167 |
| 5,147,373 | 9/1992 | Ferzli | 606/144 |
| 5,147,380 | 9/1992 | Hernandez et al. | 606/207 |
| 5,176,695 | 1/1993 | Dulebohn | 606/170 |
| 5,184,625 | 2/1993 | Cottone, Jr. et al. | 606/206 |
| 5,190,541 | 3/1993 | Abele et al. | 606/50 |

OTHER PUBLICATIONS

Product Brochure "Laparomed Electrosurgical Device," Laparomed Corporation, ©Laparomed 1991.

*Primary Examiner*—Stephen C. Pellegrino
*Assistant Examiner*—Michael Peffley
*Attorney, Agent, or Firm*—Townsend and Townsend Khourie and Crew

[57] ABSTRACT

The invention provides an actuator handle useful in connection with a variety of surgical instruments, in particular, least invasive surgical instruments having an elongate shaft and an axial passage in the shaft in which a linkage is slidably disposed. In a preferred embodiment, the actuator handle comprises a tubular housing axially aligned with the shaft having an axially-aligned elongate opening on a lateral side thereof. A lever is disposed in the elongate opening and is pivotally coupled to the housing at a first end and coupled to the linkage of the surgical instrument at a second end. The second end of the lever is coupled to the linkage wherein the linkage is translated axially by pivoting the lever relative to the housing. The actuator handle further includes a locking lever to lock the lever in an inward position, as well as a pigtail connector for connecting the linkage to an electrosurgical generator. In an exemplary embodiment, the actuator handle will be utilized in an electrosurgical instrument having a surgical hook at its distal end and a paddle element mounted to reciprocate axially relative to the hook. The paddle element and/or the hook will be electrically conductive, whereby electrical energy may be delivered from an electrosurgical generator through the hook or paddle element to a body structure. The handle further allows the paddle element to be locked in a distally-extended position for use as a paddle-shaped monopolar electrode by locking the lever in an inward position.

31 Claims, 9 Drawing Sheets

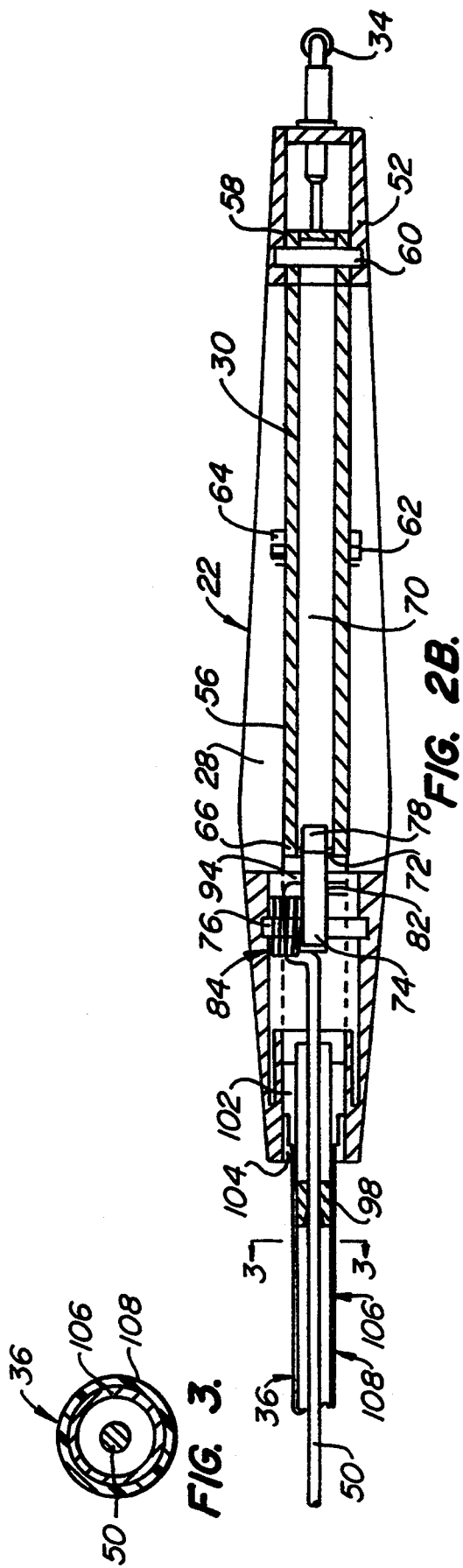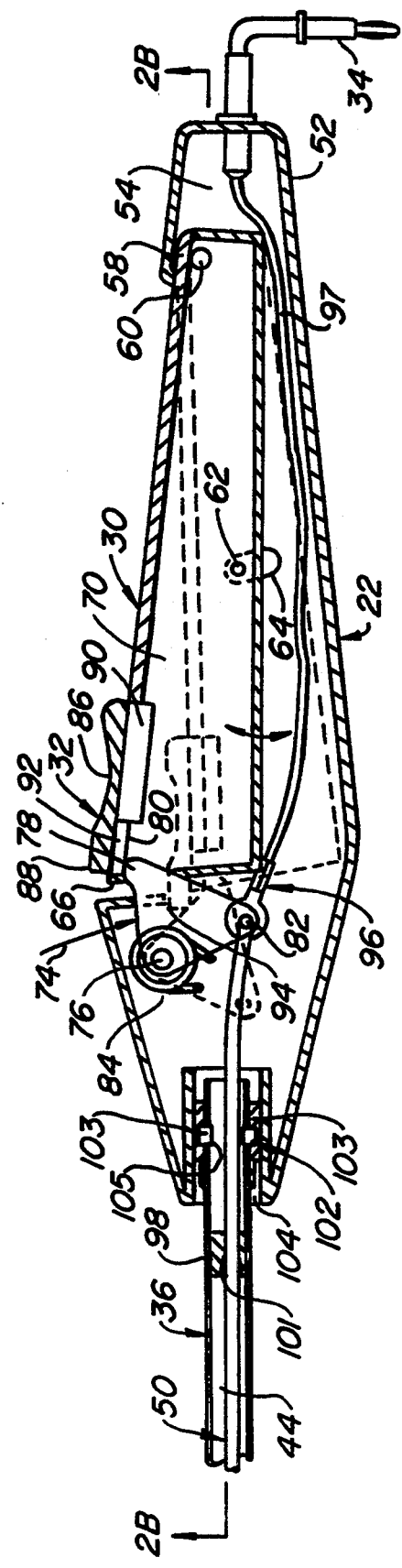

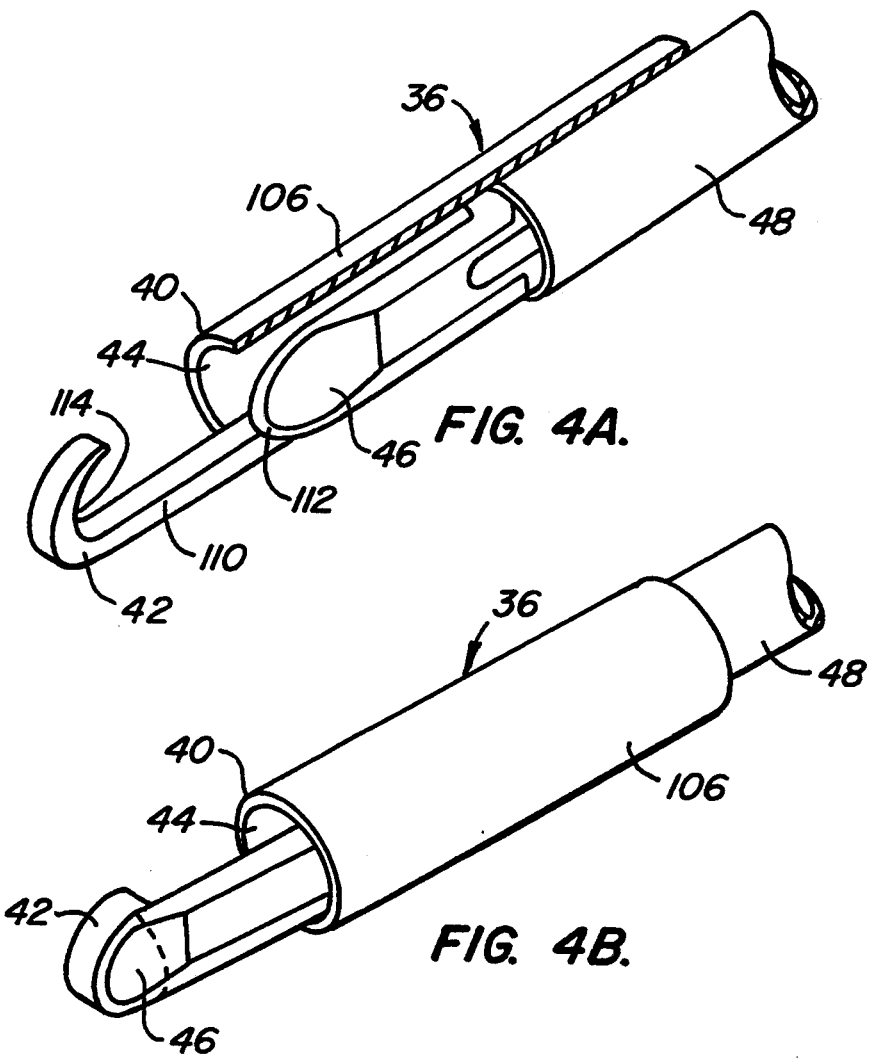
FIG. 4A.
FIG. 4B.
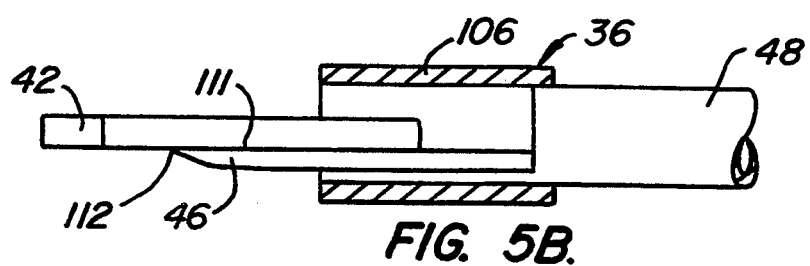
FIG. 5B.
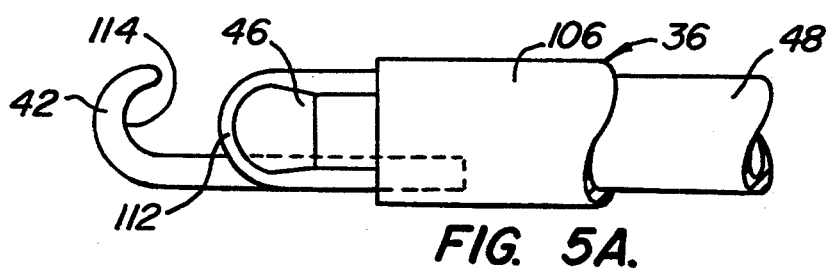
FIG. 5A.

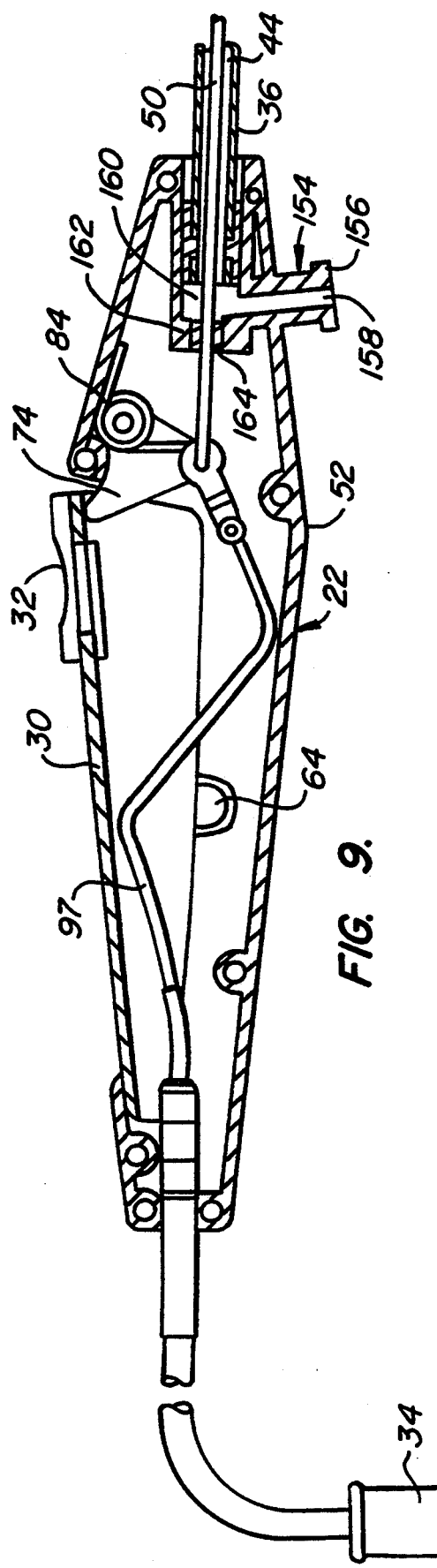
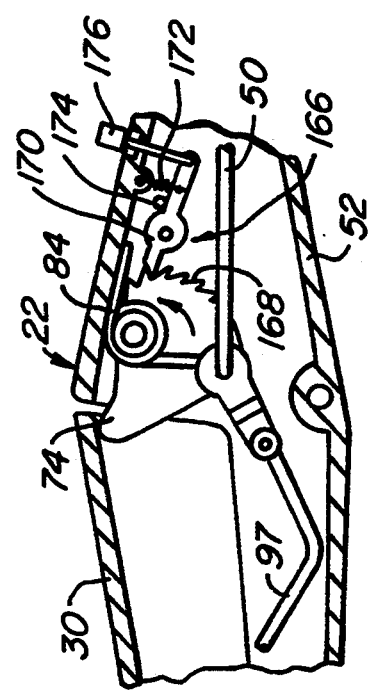
FIG. 9.
FIG. 10.

HANDLE FOR LAPAROSCOPIC INSTRUMENT

BACKGROUND OF THE INVENTION

The present invention relates generally to the structure and use of surgical instruments. More particularly, the present invention relates to an actuator handle for surgical instruments, in particular, electrosurgical and other interventional instruments for use in least invasive surgical procedures.

Least invasive surgical (LIS) techniques, such as laparoscopy, endoscopy, artheroscopy, thoracoscopy, and pelviscopy, are generally performed through small incisions using specialized instruments to perform desired surgical procedures. Usually, the instruments are introduced through a tube, such as a cannula or trocar sleeve, while the physician observes manipulation of the instruments through specialized imaging equipment, such as laparoscopes, endoscopes, thoracoscopes, and artheroscopes. Such LIS techniques offer significant advantages over conventional "open" surgical procedures. In particular, the LIS techniques are usually less traumatic, require a shorter recovery time, and are less costly than the corresponding conventional surgical techniques.

During LIS procedures, it is frequently necessary to cauterize, sever, ablate or otherwise manipulate tissue using an electrosurgical instrument. Electrosurgical instruments apply electrical energy to body tissue to change the structure or function of the tissue or body organ. Typically, electrosurgical devices apply very high frequency current to excise tissue and/or close small bleeding blood vessels by electrocauterization. Of particular interest to the present invention are monopolar electrosurgical devices, where the patient is grounded and very high frequency electrical current is applied to a body organ or a desired area of tissue using a specialized electrode. Electrosurgical procedures are particularly advantageous since they reduce bleeding from small blood vessels, facilitating the handling of highly vascularized tissues while minimizing exposure of the patient to shock and pain.

Of further interest to the present invention are electrosurgical instruments having reciprocating elements at their distal end to facilitate cauterization and/or cutting of tissue. Electrosurgical instruments having a surgical hook at their distal end with a paddle element mounted to axially reciprocate relative to the hook are described in co-pending application Ser. No. 07/692,809, assigned to the assignee of the present invention, the complete disclosure of which is incorporated herein by reference. In such devices, a body structure may be positioned within the surgical hook, which is electrically coupled to an electrosurgical generator. Electrical energy may be applied through the hook to the body structure to effect cauterization or cutting. At the same time, the paddle element may be axially reciprocated relative to the hook to engage the body structure. The paddle element may also be coupled to the electrosurgical generator, allowing electric current to be delivered to the body structure through the paddle element as well as the hook. The paddle element may thereby be used to assist in the cutting or cauterization of tissue. The paddle element is further useful in providing a flat, paddle-shaped electrode surface useful for cauterizing, cutting, or otherwise manipulating various tissue structures. In addition, the paddle element is useful for cleaning charred tissue and other debris from the surgical hook by reciprocating the paddle element relative to the hook to engage and remove such debris.

In electrosurgical instruments like those just described, a handle is provided at the proximal end of the device which can be grasped by the surgeon to position, manipulate and actuate the device. Such a handle desirably has a shape and size suitable for grasping with a single hand, and must include both an actuator for reciprocating the paddle element, as well as pigtail connector to connect the surgical hook and/or paddle element to an electrosurgical power supply. In addition, such handles may include an aspiration port for aspirating the treatment site or delivering a therapeutic agent, flushing liquid or other fluid through the device to the treatment site.

Additional LIS instruments of interest to the present invention are fascia cutters such as those described in copending application Ser. No. 07/757,170, assigned to the assignee of the present invention, the complete disclosure of which is incorporated herein by reference. Such fascia cutting instruments are used for various purposes including enlargement of abdominal penetrations and other surgical incisions through the fascia transversalis. Such enlargement is sometimes necessary during laparoscopic cholecystectomy procedures, where the gallbladder is surgically severed and withdrawn through a small cannula. Complications sometimes arise when the gallbladder is enlarged or contains gallstones which are too large to be drawn through the cannula. In such cases, it is necessary to remove the cannula and to enlarge the abdominal penetration so as to allow the gallbladder to be withdrawn through the penetration. The fascia cutting instrument described in co-pending application Ser. No. 07/757,170 comprises an elongate shaft having a transverse slot near its distal end in which the fascial layer may be received. The instrument has an axially reciprocating blade which may be translated across the slot to sever the fascial tissue, resulting in an enlarged penetration. The instrument includes a handle at its proximal end which is gripped by the surgeon to position the shaft in the penetration and manipulate the slot about the fascial layer. An actuator is coupled to the handle for selective reciprocation of the blade. The blade may further be coupled to an electrosurgical generator through pigtail connector on the handle to provide cauterization and enhanced cutting.

In addition to the instruments just described, any type of LIS or conventional surgical instrument which utilizes a handle for grasping and manipulating the instrument, as well as an actuator on the handle for selectively actuating the moving components of the device will be of interest to the present invention. Such instruments include, for example, surgical scissors, graspers, retractors, needle holders and the like.

The use of surgical instruments like the forementioned during LIS procedures can be problematic due to the difficulty in positioning and manipulation such instruments within a body cavity through a trocar sleeve or other cannula. In order to reach the area of interest, such instruments frequently have elongated shafts which can be inserted through a cannula and which have sufficient length to reach the treatment site. However, such elongated instruments are difficult to maneuver smoothly and precisely. In addition, once an instrument has been positioned near the treatment site, the surgeon must actuate the device, typically by moving a lever, trigger, slide or other such actuator on the handle of the device. Current handle designs for LIS instruments frequently require the surgeon to change hand positions to manipulate and actuate the device. Moreover, known LIS instrument handles frequently employ actuators which require awkward hand position for actuation at the various angles at which such instruments may be disposed during a procedure. In addition, current handle designs often include laterally protruding hand grips, levers, triggers and the like, which can interfere with personnel and equipment in the vicinity of the device.

For these and other reasons, an actuator handle for LIS instruments is desired which will overcome the problems of known handle designs. In particular, the actuator handle should be ergonomically designed to facilitate a firm and convenient grip on the device at various angles. The actuator handle should employ an actuator which is operable using natural hand positions, in particular, hand positions which may also be used to manipulate and position the device, obviating the need for frequent changes of hand position. The actuator should further be integrated into the handle with minimal protrusion, so as to minimize interference with personnel or equipment in the vicinity. Particularly desirable is an actuator handle which is useful in connection with electrosurgical instruments, particularly those having a movable or reciprocating element in addition to a bipolar or monopolar electrode. For use with such instruments, the actuator handle should have means for connecting the electrode to an electrosurgical power supply, as well as an actuator for actuating the movable element. The actuator handle should be further adaptable for use in fascia cutting instruments. The actuator handle should not be limited to electrosurgical or fascia cutting devices, however, and should be useful in connection with a variety of LIS and conventional surgical instruments.

SUMMARY OF THE INVENTION

The invention provides an ergonomically designed actuator handle for use with a variety of surgical instruments, having particular usefulness in LIS instruments. The actuator handle is particularly adapted for use in electrosurgical instruments having reciprocating elements as well as monopolar or bipolar electrodes. The actuator handle facilitates firm gripping of the surgical instrument at natural hand positions convenient for manipulating and positioning such instruments through a small incision or cannula. Further, the actuator handle provides an actuator lever axially aligned with the handle and conveniently nested in the handle housing for a streamlined, unobtrusive design with natural and convenient actuator motion. The actuator handle further provides means for electrical connection to an electrosurgical generator. Moreover, the actuator handle provides gaseous sealing means for use in LIS techniques in which the body is insufflated with an insufflation fluid, eliminating leakage through the LIS instrument.

The actuator handle of the invention will find its greatest use in surgical instruments having an elongate shaft with an axial lumen between the distal and proximal ends of the shaft, the instrument having interventional means, such as a monopolar electrode or tissue dissection blade, at the distal end of the shaft and a linkage disposed in the axial lumen coupled to the interventional means. The actuator handle will comprise a tubular housing secured to the proximal end of the shaft generally aligned with the axial lumen and having an elongate opening on a lateral side. A lever is disposed in the elongate opening and has a first end pivotally coupled to the housing and a second end opposite the first end. Means are provided in the housing for coupling the second end of the lever to the linkage of the instrument, such that the lever is pivotable relative to the housing between an outward position and an inward position so as to axially reciprocate the linkage.

Preferably, the actuator handle will further include means for locking the lever in the inward position, providing two linkage positions at which the user need not maintain pressure on the lever. In one embodiment, the locking means comprises a thumb switch slidably mounted to the lever which may be translated distally into an aperture in the housing when the lever is in an inward position.

In an exemplary embodiment, the means for coupling the second end of the lever to the linkage will comprise a bellcrank pivotally coupled to the housing at a first point and pivotally connected to the linkage at a second point. The bellcrank will further have a contact surface separated from the first and second points for slidably engaging the second end of the lever. In this way, movement of the lever relative to the housing will pivot the bellcrank about the first point, thereby translating the linkage axially through the axial lumen in the shaft.

The actuator handle may further include means in the housing for gaseously sealing the axial lumen of the shaft. Such sealing means will prevent leakage of insufflation gas from a body cavity. In an exemplary embodiment, the sealing means will comprise a cylindrical polymeric seal disposed about the linkage at the proximal end of the shaft.

The invention further provides an electrosurgical device comprising an elongate shaft having distal and proximal ends with an axial lumen therebetween. A surgical hook and a paddle element are disposed at the distal end of the shaft, and means are provided for mounting the surgical hook and paddle element to the shaft so as to axially reciprocate relative to each other. A linkage is slidably disposed in the axial lumen of the shaft and coupled to the means for mounting the surgical hook and paddle element. A tubular housing generally aligned with the axial lumen has a distal end attached to the proximal end of the shaft, a proximal end opposite the distal end, and an axially-aligned elongate opening on a lateral side thereof. A lever is disposed in the elongate opening, the lever having a first and pivotally coupled to the housing and second end opposite the first end. Means are further provided in the housing for coupling the second end of the lever to the linkage, such that the lever is pivotable relative to the housing between an outward position and an inward position so as to axially reciprocate the paddle element relative to the hook element.

Usually, the paddle element and the hook will be electrically coupled to the distal end of the shaft, and the shaft will have an electrically insulating cover from its proximal end to its distal end. Preferably, the linkage will comprise an electrically conductive rod coupled to the paddle element, and pigtail connector will be coupled to the proximal end of the rod for connection to an electrosurgical power supply.

In a further preferred embodiment, the electrosurgical device will include means for locking the lever in the inward position, such that the paddle element is distally extended. This permits the paddle element to be used as a monopolar electrode for cauterization or dissection without requiring the user to maintain the lever in the inward position. In one embodiment, the locking means comprises a thumb switch slidably mounted on the lever so as to engage the handle housing sliding the thumb switch distally.

In one exemplary embodiment, the surgical hook will have a laterally-facing surface and a proximally facing surface, and the paddle element will be axially slidable along the laterally facing surface so that a distal end of the paddle engages the proximally facing surface of the hook. In this embodiment, the distal end of the paddle will usually have a sharpened edge to assist in cutting tissue.

In an alternative embodiment, the surgical hook will have at least one planar face and the paddle element will have at least one planar surface disposed to shear against the planar face of the hook. The surgical hook may include two planar faces on opposite sides thereof and the paddle element may be forked and include two plates each having a planar surface disposed to shear against the planar faces on either side of the hook.

The invention further provides an electrosurgical method comprising the steps of introducing an axial shaft of an electrosurgical device to an internal body location; positioning a body structure in a surgical hook at a distal end of a shaft; pivoting an axially aligned lever coupled to a tubular housing at a proximal end of the shaft from an outward position to an inward position to translate a paddle element along the shaft relative to the hook; and supplying electric current to the paddle element and/or the hook to sever and/or cauterize the body structure.

The method may further comprise locking the lever in the inward position by sliding a thumb switch on the lever to engage the housing, so that the paddle element is maintained in a distally extended position. The method may then include the step of delivering electrical energy to tissue through a lateral surface of the paddle element with the lever locked in the inward position.

A further understanding of the nature and advantages of the invention may be realized by reference to the remaining portions of the specification and drawings.

BRIEF DESCRIPTION OF THE DRAWINGS

FIGS. 2A and 2B are side and top cross-sectional views, respectively, of an actuator handle for a surgical instrument constructed in accordance with the principles of the present invention.

FIG. 3 is a transverse cross-sectional view through the shaft coupled to the actuator handle of FIGS. 2A and 2B.

FIGS. 4A and 4B are perspective views of a distal end of the electrosurgical device of FIG. 1.

FIGS. 5A and 5B are front and top partial cross-sectional views, respectively, of the distal end of the electrosurgical device of FIG. 1.

FIG. 9 is a side cross-sectional view of a further embodiment of an actuator handle constructed in accordance with the principles of the present invention.

FIG. 10 is a partial side cross sectional view of yet another embodiment of an actuator handle constructed in accordance with the principles of the present invention.

DESCRIPTION OF SPECIFIC EMBODIMENTS

The present invention provides an actuator handle useful in connection with a variety of surgical instruments, with particular usefulness in LIS instruments. While the handle will be described in connection with electrosurgical devices for cauterizing and cutting tissue, fascia cutting instruments for enlarging a penetration through the fascial layer as well as surgical scissors, it will be understood that the actuator handle of the present invention may be adapted for use in a variety of both LIS and conventional surgical instruments which utilize a handle for gripping and manipulation by the surgeon and an actuator for selectively actuating the movable components in such devices.

The actuator handle of the invention is ergonomically designed for maximum device control, comfort and convenience. The actuator handle has a streamlined design, having a tubular structure which is axially aligned with the elongate shafts typical of LIS instruments, without lateral protrusions which may interfere with personnel or equipment in the vicinity. The actuator handle utilizes an actuation lever axially aligned and nested within the handle housing which is easily actuated in various hand positions, eliminating the need for frequent changes of hand position. Particularly useful is the locking feature of the actuator handle, wherein the actuation lever may be locked in position so that the moving components of the device, for example, an electrosurgical paddle element, will be maintained in an extended position. In this way, the instruments may be used in two or more configurations which do not require the surgeon to maintain pressure on the actuation lever. The actuator handle further provides electrical connection between the electrodes of an electrosurgical device and an electrosurgical generator.

Figure 1:
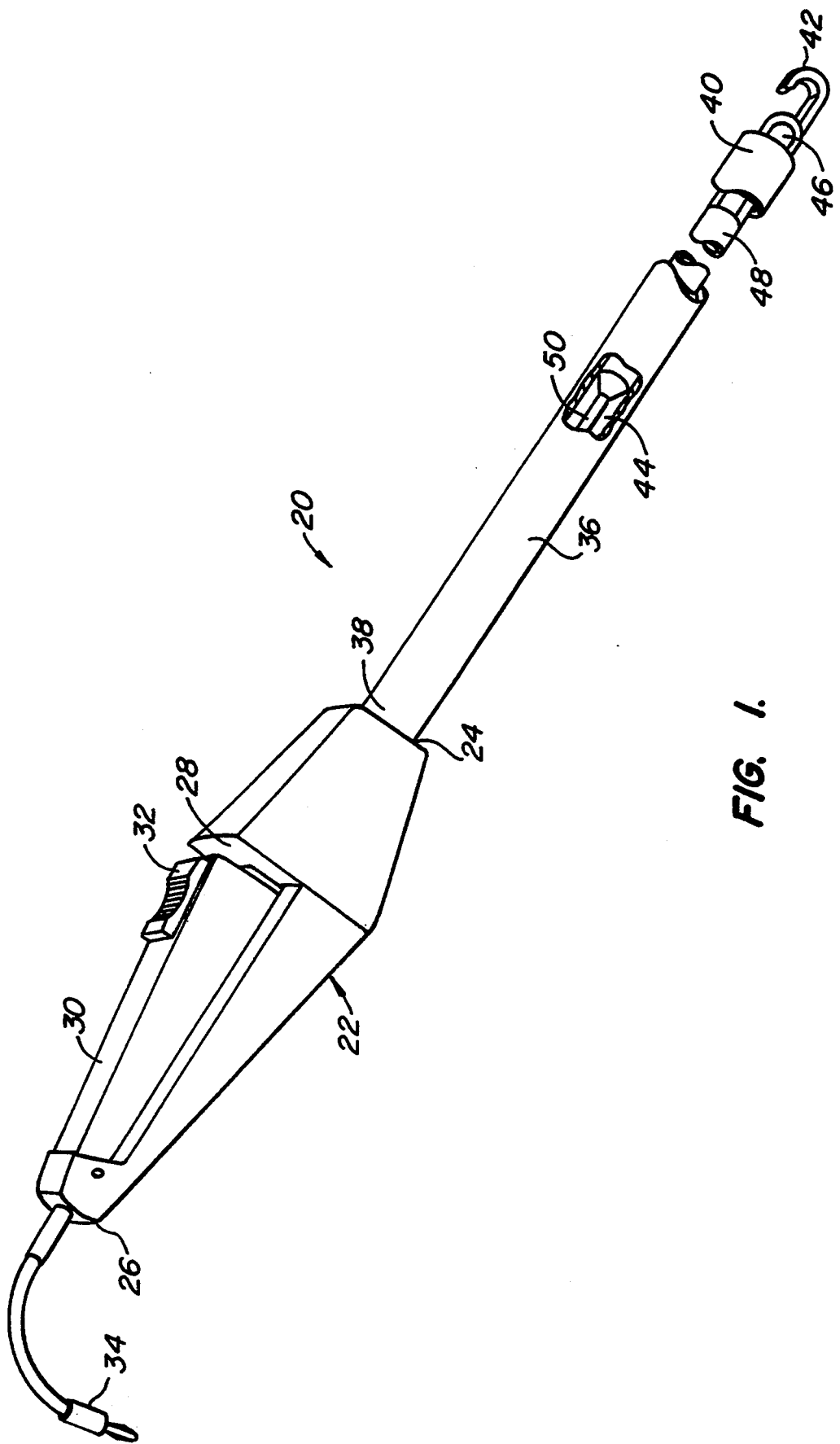
FIG. 1 is a perspective view of an electrosurgical device constructed in accordance with the principles of the present invention.
Figure 6A:
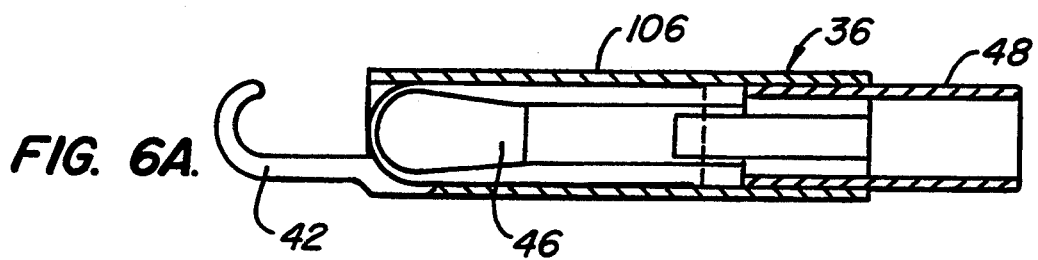
FIGS. 6A-6D are front and top partial cross-sectional views of an alternative embodiment of the distal end of the electrosurgical device of FIG. 1, showing the paddle element in a retracted position and an extended position.
Figure 6B:
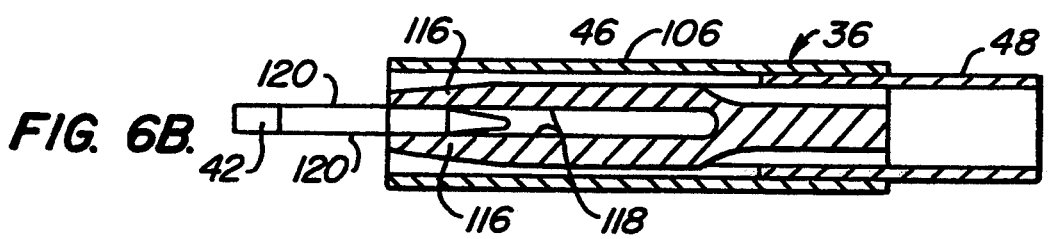
Figure 6C:
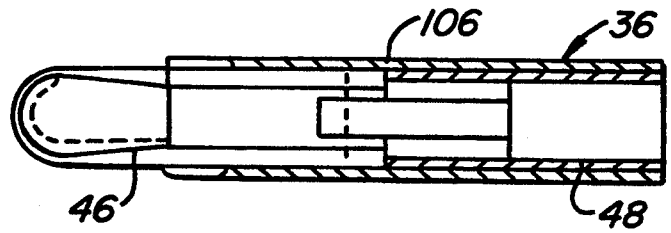
Figure 6D:
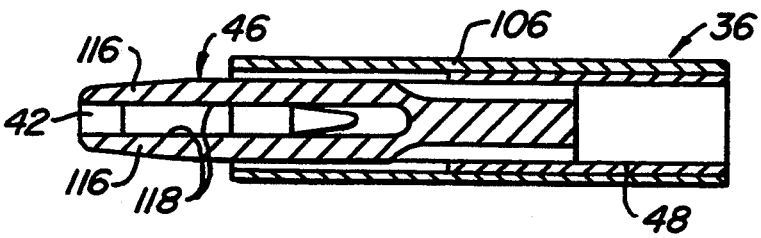

An electrosurgical device employing an actuator handle constructed in accordance with the principles of the present invention will be described in connection with FIGS. 1-7. Referring to FIG. 1, electrosurgical device 20 has an actuator handle 22 having a distal end 24 and a proximal end 26. The handle has an opening or aperture 28 on a lateral side in which is disposed a pivotable lever 30. Lever 30 has a thumb switch 32 slidably disposed on a lateral surface of the lever. Actuator handle 22 further includes pigtail connector 34 suitable for connection to an electrosurgical generator.

An elongate shaft 36 has a proximal end 38 coupled to the distal end 24 of actuator handle 22. A surgical hook 42 is secured to distal end 40 of shaft 36. Shaft 36 further includes an axial lumen 44 extending from the proximal end to the distal end of the shaft. At the distal end, a paddle element 46 is slidably disposed in the axial lumen. Paddle element 46 is fixed to the end of an actuator shaft 48 slidably disposed in axial lumen 44 and connected to a linkage rod 50 extending through axial lumen 44 into actuator handle 22.

Referring now to FIGS. 2A and 2B, actuator handle 22 comprises a housing 52, which may be formed from an electrically insulating material, such as acrylonitrile-butadiene-styrene (ABS), polycarbonate, Delrin® (an acetyl resin), or the like. Housing 52 will have an elongate tubular construction, with round, partially round, rectangular or other cross-sectional shape suitable for gripping with a single hand. Tubular housing 52 will define an open interior 54 generally aligned with the axial lumen 44 of shaft 36. Aperture 28 will be formed on a lateral side of housing 52 and will have an axially aligned slot 56 which opens into interior 54 of the housing. Lever 30 will be axially disposed in slot 56 with a lateral longitudinal portion of the lever exposed in aperture 28. A proximal end 58 of the lever will be pivotally coupled to housing 52 by means of a pin 60. The distal end 66 of lever 30 is pivotable about an axis perpendicular to the axial direction (defined by shaft 36) from an outward position to an inward position (shown in phantom) in the interior of housing 52. In a mid portion of lever 30, cylindrical heads 62 extend outward from the sides of lever 30 and reside in guide channels 64 in the sidewalls of housing 52. The inward and outward movement of lever 30 is thereby limited by the engagement of heads 62 against the ends of channel 64.

Lever 30 has an open interior 70 and a vertical slot 72 along its distal side. A bellcrank 74 is pivotally mounted in the interior of housing 52 distally of lever 30 by means of a pin 76. Bellcrank 74 is generally triangular and pivots about pin 76 which extends through a first of the points of the bellcrank. At a second point, bellcrank 74 has a rounded contact surface 78 extending through slot 72 in the lever which slides against an interior surface 80 of lever 30. A third point 82 of bellcrank 74 has a transverse bore through which the proximal end of linkage rod 50 extends.

In a preferred embodiment, linkage rod 50 will comprise a flexible rod of stainless steel or the like, which is laterally deflectable while having sufficient axial rigidity to actuate paddle element 46 at the distal end of the shaft. In this way, as lever 30 is pivoted from an outward to an inward position, contact surface 78 is engaged by interior surface 80 of the lever, rotating the bellcrank about pin 76 and translating linkage rod 50 axially through shaft 36. As shown in FIG. 2B, the proximal end of linkage rod 50 is formed in a J or L shape to provide clearance for the bellcrank and to attain a transverse orientation to extend through transverse bore 82 in the bellcrank. A torsion spring 84 is further provided about pin 76 to urge bellcrank 74 in a counterclockwise direction, biasing lever 30 in an outward position.

The invention further includes means for locking lever 30 in the inward position, which, in an exemplary embodiment, comprises a thumb switch 32 slidably mounted to lever 30 near the distal end 66 thereof.

Thumb switch 32 includes a surface contour 86 configured for engagement by the thumb. Usually, the surface contour will have transverse grooves or ridges to facilitate non-slip engagement. An extension portion 88 extends distally from surface contour 86. The thumb switch further includes a sliding retainer portion 90 which resides in a slot 92 disposed axially through the lateral sidewall of lever 30. Thumb switch 32 is thereby configured to slide axially along lever 30 with retainer portion 90 sliding in slot 92. When lever 30 is in the inward position (shown in phantom), thumb switch 32 may be moved distally so that extension portion 88 is received in a slot or aperture 94 in a distal portion of the housing, locking the lever in the inward position.

In a preferred embodiment, linkage rod 50 will comprise an electrically conductive material and will be connected at its proximal end to an electrical coupling 96 in housing 52. Electrical coupling 96 will be connected by means of a wire 97 to pigtail connector 34, for connection to an electrosurgical generator.

In a further aspect of the invention, actuator handle 22 will include sealing means 98 for gaseously sealing the proximal end of axial lumen 44 in shaft 36. In a preferred embodiment, sealing means 98 will comprise a cylindrical polymeric seal of a material such as silicone disposed near the proximal end of shaft 36 about linkage 50. Seal 98 has an axial bore 101 through which linkage rod 50 may extend in sealable contact with the interior of the seal. In this way, seal 98 provides a gas-tight seal in the proximal end of the shaft, preventing leakage of insufflation gas through the axial lumen into the handle.

Shaft 36 will be mounted to actuator handle 22 by means of a collar assembly 102 disposed in a distal aperture 104 in housing 52. Collar assembly 102 will preferably comprise a pair of split halves 103 each having an inward extending protrusion 105 which extends through one of a pair of transverse holes in shaft 36. Usually, collar 102 will be solvent bonded to the housing within aperture 104, securing shaft 36 to the handle.

In an exemplary embodiment, pigtail connector 34 will include a 3/32 inch diameter plug connector of standard configuration. It will be connected to commercially available electrosurgical power supplies such as those available from vendors such as Valley Lab, Inc. (A Pfizer Company), Boulder, Colo.; Aspen Labs, Inc. (A Conmead Company), Inglewood, Colo.; Birtcher Corp., Irvine, Calif.; and Bard Electromedical Systems, Inc., Inglewood, Colo.

Referring now to FIGS. 2B and 3, shaft 36 will preferably comprise rigid, electrically conductive tubing 106, covered by an electrically insulating sleeve or cover 108. In an exemplary embodiment, tubing 106 will be surgical stainless steel, while insulating sleeve 108 will be a polymeric material such as polyethylene. The dimensions of the shaft 36 are not critical, but the diameter will usually be sufficiently small to allow for passage through a conventional cannula, usually being 5 mm or less in diameter. The shaft will be sufficiently long to permit access by the distal tip to any desired location in the body, typically having a length in the range from about 25 cm to 38 cm.

Referring now to FIGS. 4A-4B and 5A-5B, a distal portion of shaft 36 will be described. For purposes of illustration, the insulating cover 108 (FIG. 3) on shaft 36 is not shown in FIGS. 4-7, however it will be understood that the insulating sleeve will cover the exterior of the shaft up to distal end 40. Surgical hook 42 is composed of an electrically conductive material such as surgical stainless steel and is secured to the distal end of tubing 106. A paddle element 46 is secured to actuator shaft 48 and may be axially reciprocated relative to surgical hook 42. Actuator shaft 48, linkage 50, as well as paddle element 46 will also be electrically conductive, typically being stainless steel. Actuator shaft 48 will preferably be in sliding engagement with tubing 106 in axial lumen 44, and paddle element 46 in sliding engagement with the hook 42, to provide electrical connection therebetween. In this way, electrical current delivered through linkage 50 will be conducted to paddle element 46 as well as hook 42.

In a first embodiment, a single paddle element is disposed adjacent a flat lateral face 110 of hook 42. Paddle element 46 has a flat surface 111 disposed to slide against face 110. In this way, paddle element 46 may be shifted from a retracted position, shown in FIG. 4A, to an extended position, shown in FIG. 4B, by actuating lever 30 on actuator handle 22.

Axial translation of paddle element 46 past surgical hook 42 has several advantages. First, a leading edge 112 of paddle element will cooperate with an inner edge 114 of hook 42 to provide a shearing action as the paddle element is moved forward. Thus, when tissue or other body structure is held within hook 42, the shearing action of the paddle 46 may enhance dissection afforded by the electric current. Additionally, the motion of the paddle element 46 past the surgical hook 42 will be able to clean char and other tissue from the hook which may adhere to the hook during use.

FIGS. 6A-6D illustrate an alternative embodiment of paddle element 46 in the electrosurgical device of the present invention. In this embodiment, paddle element 46 comprises a forked end having a pair of parallel plates 116 each having a flat surface 118 which slides against flat faces 120 on either side of hook 42. Such a configuration provides a double shearing action on a body structure received in hook 42 and further serves to apply balanced forces to the tissue structure on either side of hook 42 for effective tissue dissection.

Figure 7A:
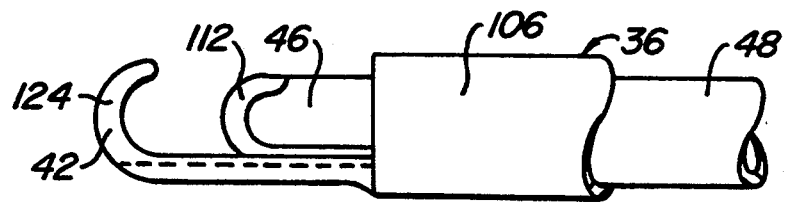
FIGS. 7A and 7B are front and top partial cross-sectional views, respectively, of a further alternative embodiment of the distal end of the electrosurgical device of FIG. 1.
Figure 7B:
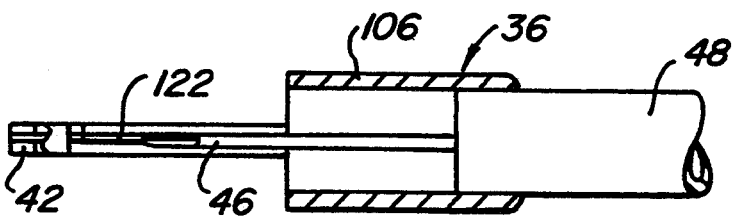

Still another embodiment of the electrosurgical device of the invention is shown in FIGS. 7A and 7B. In this embodiment, paddle element 46 is axially aligned with hook 42 and slides in an axial channel 122 in the hook. Channel 122 will preferably extend into the distal J-shaped portion 124 of the hook to permit leading edge 112 of the paddle element to extend at least partially into the channel in distal portion 124. In this way, paddle element 46 enhances tissue dissection by urging the tissue within hook 42 against the distal portion 124 of the hook and penetrating leading edge 112 through the tissue.

Various other configurations of the paddle element and surgical hook, as well as other monopolar electrode structures suitable for use in the electrosurgical device of the invention, are described in co-pending application Ser. No. 07/692,809, assigned to the assignee of the present invention, the complete disclosure of which has been incorporated herein by reference.

Figure 8:
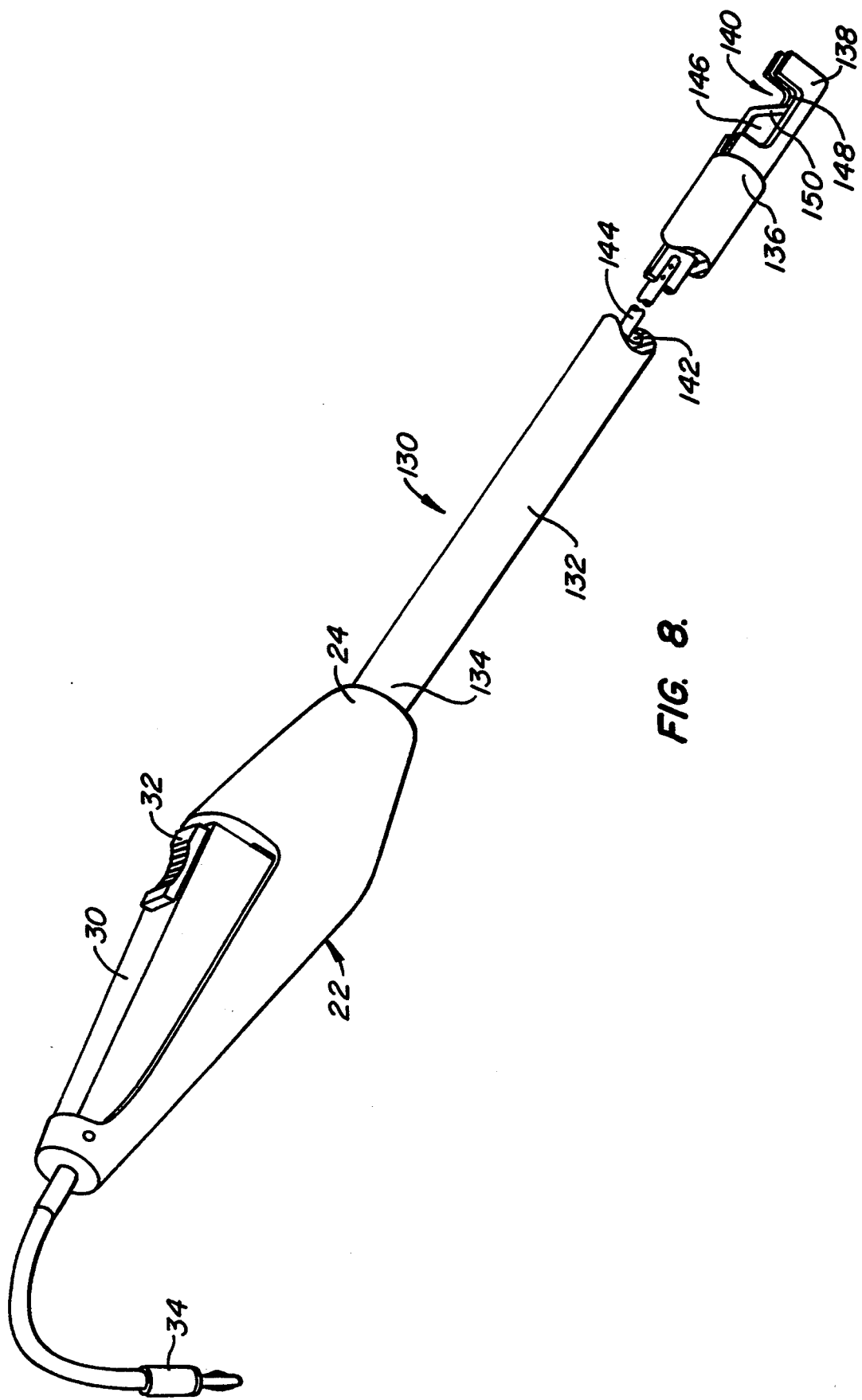
FIG. 8 is a perspective view of a fascia cutter utilizing an actuator handle constructed in accordance with the principles of the present invention.

FIG. 8 illustrates a further embodiment of the present invention wherein actuator handle 22 is incorporated in a fascia cutting instrument like that described in co-pending application Ser. No. 07/757,170, assigned to the assignee of the present invention, the complete disclosure of which has been incorporated herein by reference. Fascia cutting instrument 130 includes an elongate shaft 132 attached at its proximal end 134 to the distal end 24 of handle 22. A slotted head 138 is secured to distal end 136 of shaft 132. Head 138 defines a transverse slot 140. Shaft 132 has an axial lumen 142 in which a linkage 144 is slidably disposed. The proximal end of linkage 144 will be coupled to bellcrank 74 in handle 22. The distal end of linkage 144 is connected to the proximal end of a blade 146 which is slidable in an axial channel 148 in head 138. In this way, actuation of lever 30 in handle 22 translates linkage 144 to reciprocate blade 146 across slot 140.

Blade 146 has a tapered cutting edge 150 along its distal end. Preferably, blade 146, and linkage 144 will be an electrically conductive material such as stainless steel, and will be electrically coupled to pigtail connector 34 in handle 22. Connector 34 may be connected to an electrosurgical generator to deliver electric current through linkage 144 to blade 146 to enhance tissue dissection. As described above, lever 30 will preferably be biased in an outward position so that blade 146 is retracted within shaft 132 when lever 30 is in the outward position.

In use, the fascia cutting device of FIG. 8 will be positioned through a penetration in the fascia transversalis, and slot 140 will be positioned to receive a portion of the fascial layer. Blade 146 may then be translated axially by actuating lever 30 to sever the fascial layer, enlarging the penetration. Electric current may be delivered from an electrical generator through connector 34 to blade 146 to enhance cutting. Further aspects of fascia cutting instruments suitable for use in connection with the actuator handle of the present invention are described in co-pending application Ser. No. 07/757,170, the complete disclosure of which has been incorporated herein by reference.

FIG. 9 illustrates yet another embodiment of the actuator handle of the invention. In this embodiment, actuator handle 22 includes an aspiration/agent delivery port 154 for attachment of a suction device to aspirate the treatment site, or for attachment of an agent delivery mechanism, such as syringe or pump, to deliver a therapeutic agent or other fluid to the treatment site through axial lumen 44. Port 154 will preferably comprise a lure fitting 156 having a passage 158 in fluid connection with an interior chamber 160 defined by an annular wall 162 formed in housing 52. The proximal end of shaft 36 is disposed in chamber 160, and linkage 50 extends proximally through the chamber into the interior of the handle. A cylindrical seal 164 seals the proximal end of chamber 160 about linkage 50 to prevent leakage of fluid or insufflation gas into the handle. In this way, aspiration of the treatment site may be accomplished by applying suction through passage 158, which will draw fluid through an opening at the distal end of shaft 36 (not shown) and proximally through axial lumen 44. A therapeutic agent or other fluid may be delivered to the treatment site by delivering the agent or fluid into passage 158, from which it will flow through axial lumen 44 and an opening (not shown) at the distal end of shaft 36.

FIG. 10 illustrates an alternative embodiment of the lever locking means of the actuator handle. In this embodiment, the lever locking means comprises a ratchet mechanism 166 on bellcrank 74. Ratchet mechanism 166 includes a plurality of teeth 168 on bellcrank 74, and a pall 170 for engaging teeth 168. Pall 170 is biased in a counter clockwise direction by tension spring 172, which urges the pall against a stop 174 on housing 52. In this way, inward movement of lever 30 rotates bellcrank 74 in a counter clockwise direction such that teeth 168 are successively engaged by pall 170. At any desired lever position between the most outward and most inward positions, pressure may be released lever 30, and pall 170 will prevent clockwise rotation of bellcrank 74, maintaining the lever (and the attached interventional means at the distal end of the instrument) in position. When it is desired to return lever 30 to its outward position, a release button 176 is pressed, rotating pall 170 in a clockwise direction to disengage the pall from teeth 168, permitting clockwise rotation of bellcrank 74 under the force of torsion spring 84.

Figure 11A:
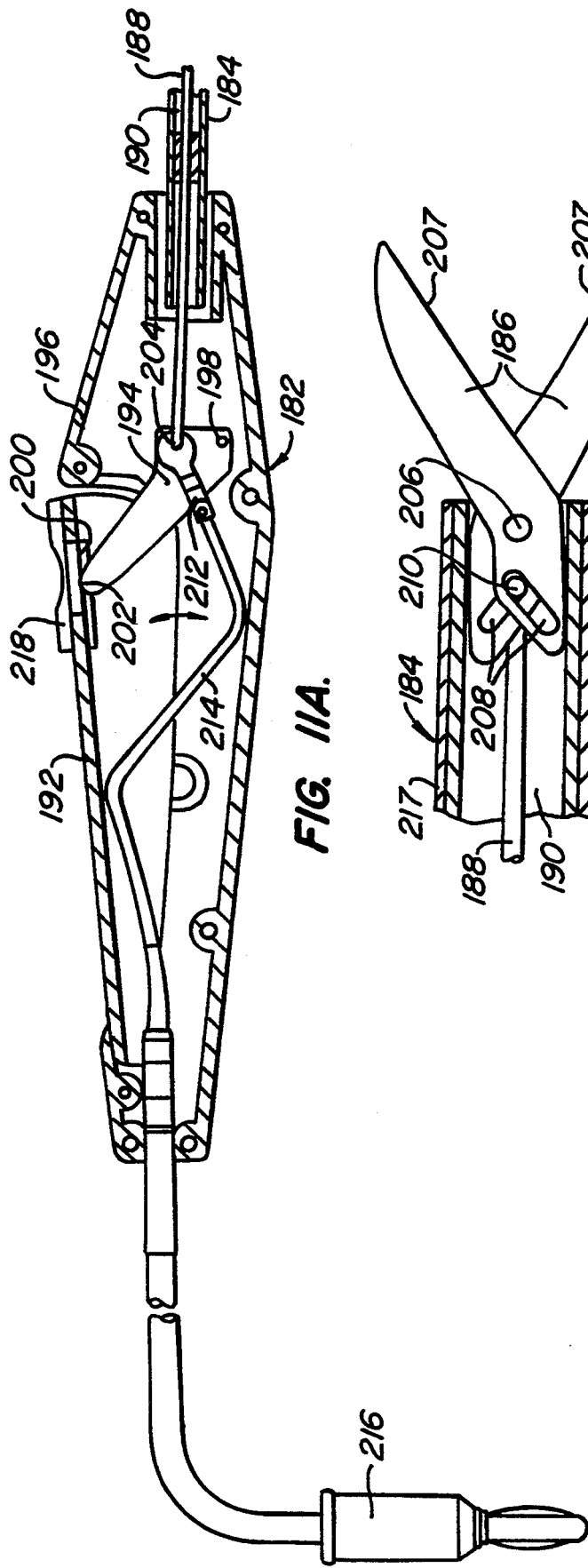
FIG. 11A is a side cross-sectional view of a further embodiment of an actuator handle in a surgical scissor instrument in accordance with principles of the present invention.
Figure 11B:
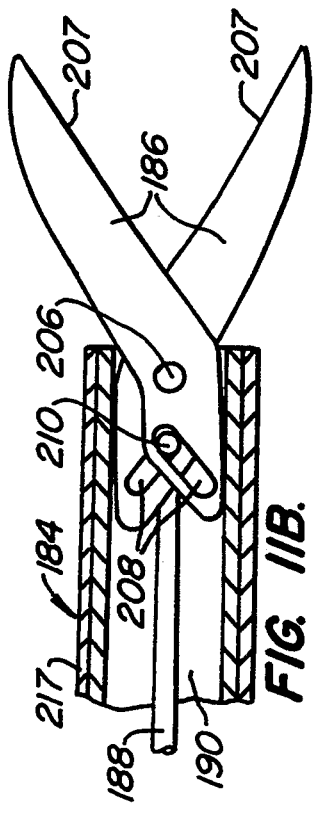
FIGS. 11B-11C are side cross-sectional views of a distal end of the scissor instrument of FIG. 11A.
Figure 11C:
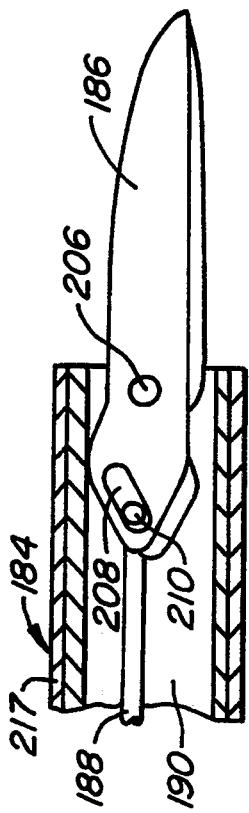

FIGS. 11A–11C illustrate a further embodiment of a surgical instrument incorporating the actuator handle of the present invention. In this embodiment, the surgical instrument comprises surgical scissors, including actuator handle 182 at the proximal end of the device, shaft 184 secured to actuator handle 182, and, as shown in FIGS. 11B–11C, reciprocating blades 186 coupled to the distal end of shaft 184. A linkage 188 is coupled to blades 186 and extends through an axial lumen 190 in shaft 184 to actuator handle 182. The proximal end of linkage 188 is coupled to lever 192 in handle 182. Actuator handle 182 is substantially the same as that described above in connection with FIGS. 1, 2A and 2B, except that the means for coupling linkage 188 to lever 192 is configured to pull linkage 188 proximally, rather than push the linkage distally as in previous embodiments. The coupling means comprises, in an exemplary embodiment, a bellcrank 194 which is pinned to handle housing 196 at pivot point 198. Bellcrank 194 slidably engages interior surface 200 of lever 192 along a curved contact surface 202. The proximal end of linkage rod 188 is coupled to bellcrank 194 at point 204. In this way, inward motion of lever 192 rotates bellcrank 194 in a counter-clockwise direction about pivot point 198, drawing linkage rod 188 in a proximal direction.

Referring to FIGS. 11B–11C, blades 186 are pivotally coupled together by a pin 206 which is secured to the distal end of shaft 184. Blades 186 have sharpened inner edges 207 and slide in shearing action against each other when the blades are closed. Each blade has an inclined slot 208 near its proximal end which overlap so as to receive a distal end 210 of linkage 188 through both slots. In this way, when linkage rod 188 is moved proximally, the movement of distal end 210 through slots 208 causes blades 186 to pivot toward each other into the position shown in FIG. 11C.

It will be appreciated that electrical energy may be applied through blades 186 to assist in tissue dissection. In this embodiment, blades 186 and linkage rod 188 will be an electrically conductive material such as stainless steel. As shown in FIG. 11A, the proximal end of linkage rod 188 is coupled to electrical coupling 212 and wire 214, which are coupled to pigtail connector 216 for connection to an electro-surgical generator. Shaft 184 is covered with an electrically insulating sleeve 217 to prevent conduction of current to tissue through the shaft.

Further, it may be seen that lever 192 may be locked in an inward position using a thumb switch 218 or other locking means as in previous embodiments. With lever 192 in a fully inward position, blades 186 will preferably be in a closed configuration as in FIG. 11C. In such a configuration, the blades have a profile sufficiently small for insertion through a trocar sleeve or other cannula. In addition, with blades 186 in a closed configuration, the device may be manipulated in the body cavity without sharp edges 207 exposed, to avoid any risk of injury. Moreover, blades 186 may be locked in the closed configuration for use as a monopolar electrode for cauterization or dissection.

Figure 12A:
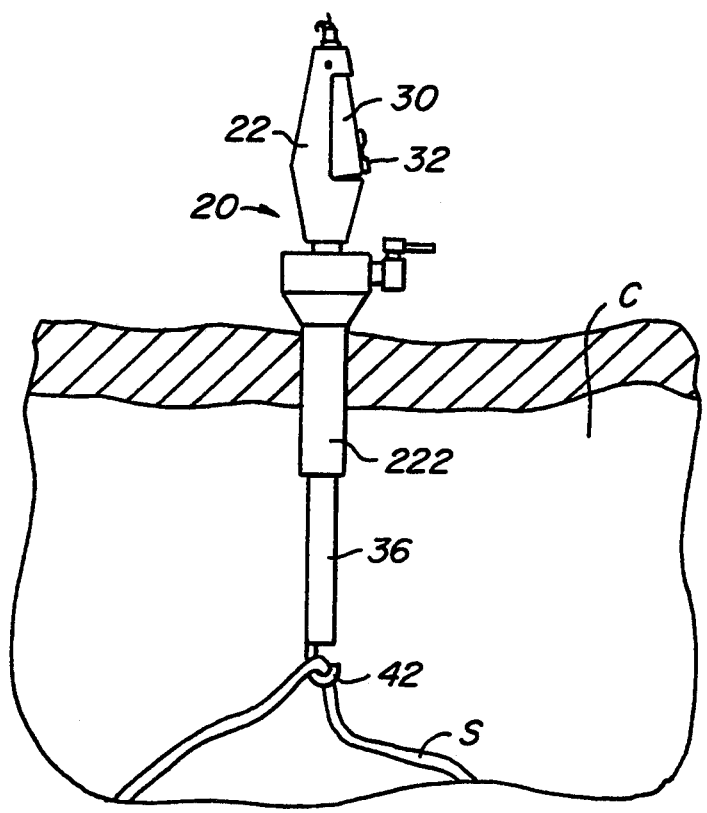
FIGS. 12A-12C are front elevational views illustrating the use of the electrosurgical device of FIG. 1 in a body cavity according to the principles of the method of the present invention.

The method of the present invention will be described with reference to FIGS. 12A–12C. The method will be described in connection with the electrosurgical device of FIGS. 1–7, however, it will be understood that the principles of the method of the invention may be applied to techniques using a variety of surgical instruments, including the fascia cutter of FIG. 8 as well as a variety of other LIS and conventional surgical instruments.

Usually, the electrosurgical device 20 will be introduced through a trocar sleeve or other cannula 222 which is positioned percutaneously to facilitate introduction of instruments through a sealed passage into a body cavity C. In laparoscopy, for example, the body cavity will comprise the peritoneal cavity, in thoracoscopy the thorax, in pelviscopy the pelvis, and so on. In some procedures, the body cavity C will be insufflated using an insufflation gas, commonly carbon dioxide, to enlarge the cavity for enhanced visualization and access. Cannula 222 will permit introduction of surgical instruments through a sealed passage which prevents leakage of insufflation gas from the body cavity.

Electrosurgical device 20 will be positioned through cannula 222 with the surgical hook 42 near the body structure S desired to be dissected, cauterized or manipulated. The surgeon will grasp handle 22 to manipulate instrument 20 axially and rotationally so as to engage body structure S within hook 42.

Figure 12B:
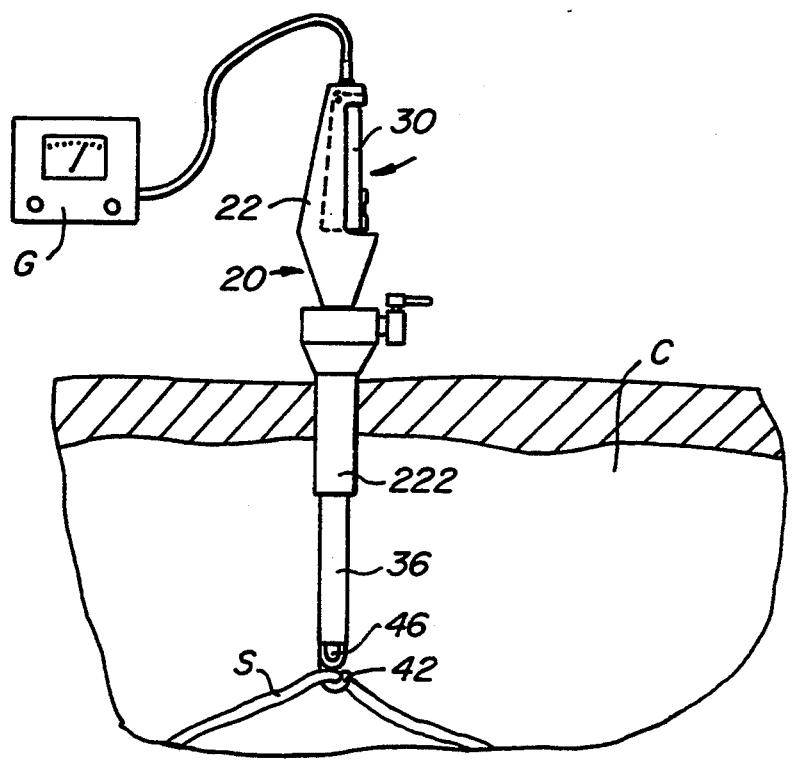

As illustrated in FIG. 12B, an electrosurgical generator G may be connected to connector 34 so as to deliver electric current to hook 42. The electric current will be passed from hook 42 to body structure S to cauterize, dissect or otherwise affect the body structure. At the same time, paddle element 46 may be extended from its retracted position in shaft 36 by pivoting lever 30 inward toward handle 22. This will cause paddle element 46 to be translated distally, sliding against hook 42. The shearing action of paddle element 46 against hook 42 will enhance dissection of body structure S. Electrical energy may also be delivered from electrosurgical generator G through paddle element 46, further enhancing dissection of the body structure. As described above, axial translation of paddle element 46 serves the additional purpose of removing char or other debris from hook 42.

Figure 12C:
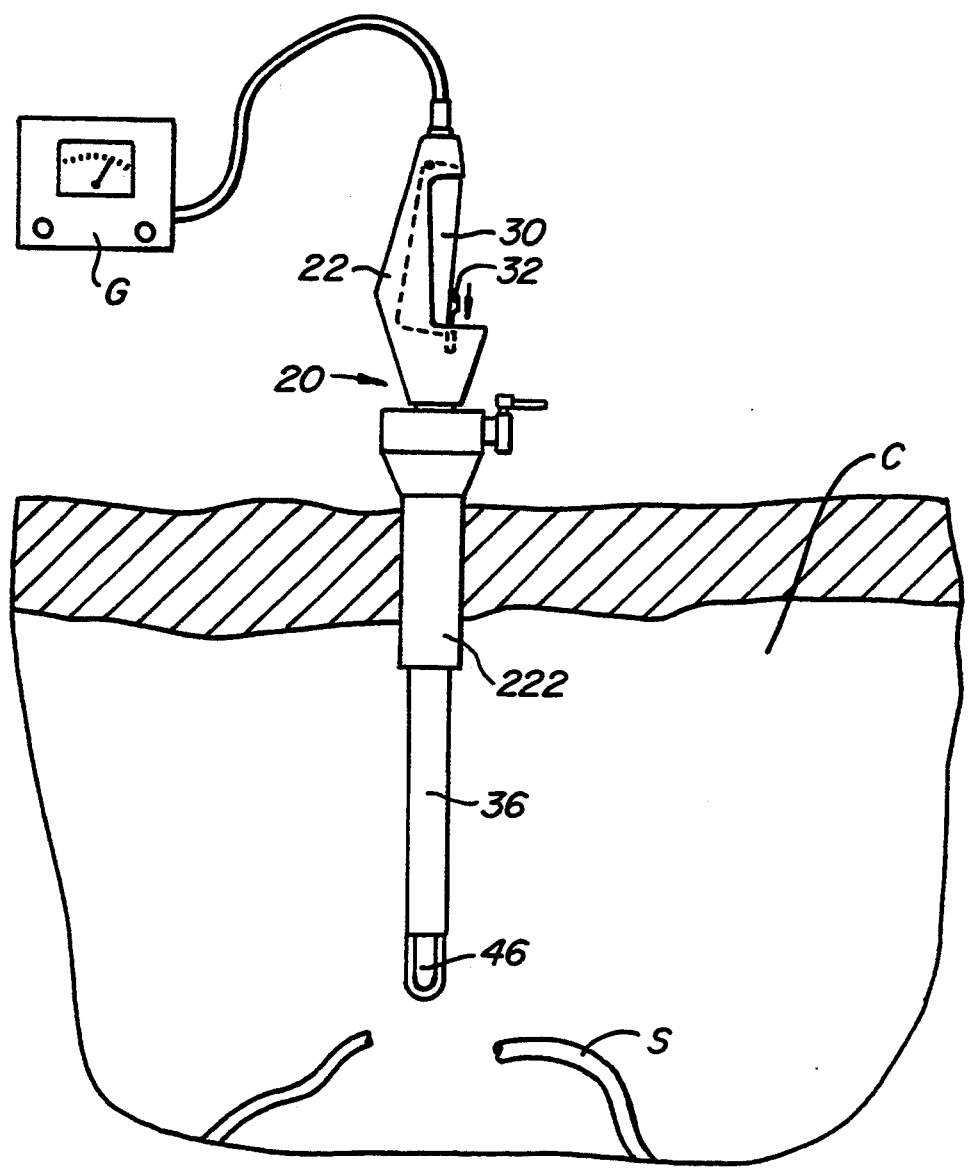

FIG. 12C illustrates the paddle element 46 in a fully extended position. With lever 30 in an inward position, thumb switch 32 may be slid distally into aperture 94 within handle 22 so as to lock lever 30 in position. In this way, paddle element 46 will remain in the distally extended position while the user is free to release pressure on lever 30. The paddle element thereby provides a wide, paddle-shaped monopolar electrode which can be used for various purposes in body cavity C, such as cauterization or dissection. The presence of paddle element 46 adjacent hook 42 further eliminates the risk of unintentionally engaging a body structure in the hook as electrosurgical device 20 is manipulated or withdrawn from the body cavity.

While the actuator handle of the present invention has been described in connection with electrosurgical devices fascia cutting instruments and surgical scissors, it will be understood that the actuator handle will be useful in connection with any of a variety of LIS and conventional surgical instruments which utilize movable components selectively actuated from a proximal end of the device. Exemplary instruments into which the actuator handle of the present invention may be incorporated include graspers, retractors, needle holders and the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An actuator handle for a surgical instrument, the surgical instrument including an elongate shaft having distal and proximal ends with an axial lumen therebetween, interventional means at the distal end and a linkage slidably disposed in the axial lumen coupled to the interventional means, the actuator handle comprising:

a tubular housing axially aligned with the shaft having a distal end attached to the proximal end of the shaft, a proximal end opposite the distal end and an axially-aligned elongate opening on a lateral side thereof;

a lever disposed in the elongate opening having a first end pivotally coupled to the housing and a second end opposite the first end, the lever being pivotable between an outward position and an inward position, the actuator handle further comprising means for biasing the lever in the outward position;

means in the housing for coupling the second end of the lever to the linkage, wherein the linkage is translated axially by pivoting the lever relative to the housing; and means for locking the lever in the inward position, the means for locking comprising a thumb switch slidably disposed on the lever near the second end, a portion of the thumb switch being axially extendable from the second end, the housing having an internal aperture disposed adjacent the second end of the lever wherein the thumb switch may be extended into the aperture when the lever is in the inward position.

2. The actuator handle of claim 1 wherein the means for coupling the lever to the linkage comprises a bellcrank pivotally coupled to the housing at a first point and pivotally connected to the linkage at a second point, the bellcrank having a contact surface for slidably engaging the second end of the lever.

3. The actuator handle of claim 1 further comprising means in the housing for gaseously sealing the axial lumen of the shaft.

4. The actuator handle of claim 3 wherein the sealing means comprises a cylindrical polymeric seal disposed about the linkage at the proximal end of the shaft, the linkage extending through the seal in contact therewith.

5. The actuator handle of claim 1 wherein the lever is coupled to the housing such that the first end is in a proximal portion of housing and the second end is in a distal portion of the housing.

6. The actuator handle of claim 1 wherein the linkage comprises an electrically conductive rod, the actuator handle further comprising means for connecting the proximal end of the rod to an electrosurgical power supply.

7. An electrosurgical device comprising:

an elongate shaft having distal and proximal ends with an axial lumen therebetween;

a surgical hook at the distal end;

a paddle element at the distal end;

means for mounting the surgical hook and the paddle element to the shaft so as to axially reciprocate relative to each other;

a linkage slidably disposed in the axial lumen of the shaft and coupled to the mounting means;

a tubular housing generally aligned with the axial lumen having a distal end attached to the proximal end of the shaft, a proximal end opposite the distal end, and an axially-aligned elongate opening on a lateral side thereof;

a lever disposed in the elongate opening, the lever having a first end pivotally coupled to the housing and a second end opposite the first end;

means in the housing for coupling the second end of the lever to the linkage, wherein the lever is pivotable relative to the housing between an outward position and an inward position to axially reciprocate the paddle element relative to the hook element; and means for locking the lever in the inward position, the means for locking comprising a thumb switch slidably disposed on the lever near the second end, a portion of the thumb switch being axially extendable from the second end, the housing having an internal aperture disposed adjacent the second end of the lever wherein the thumb switch may be extended into the aperture when the lever is in the inward position.

8. The device of claim 7 wherein the paddle element is electrically coupled to the distal end of the shaft by an electrical connection means, the shaft further having an electrically insulating cover from the proximal end to the distal end.

9. The device of claim 8 wherein the linkage comprises an electrically conductive rod coupled to the paddle element, the device further comprising a pigtail connector coupled to the proximal end of the rod for connection to an electrosurgical power supply.

10. The device of claim 7 wherein the means for coupling the second end of the lever to the linkage comprises a bellcrank pivotally coupled to the housing at a first point and pivotally connected to the linkage at a second point, the bellcrank having a contact surface for slidably engaging the second end of the lever.

11. The device of claim 7, wherein the paddle element is distally extended when the lever is in the inward position.

12. The device of claim 7 wherein the surgical hook has a laterally-facing surface and a proximally-facing surface, the paddle element being axially slidable along the laterally-facing surface so that a distal end of the paddle engages the proximally-facing surface of the hook.

13. The device of claim 12 wherein the distal end of the paddle has a sharpened edge for cutting tissue.

14. The device of claim 7 wherein the surgical hook has at least one planar face and the paddle element has at least one planar surface disposed to shear against the planar surface of the hook element.

15. The device of claim 14 wherein the surgical hook includes two planar faces on opposite sides thereof and the paddle element is forked and includes two planar surfaces disposed to shear against the planar faces of the hook.

16. The device of claim 7 further comprising means in the housing for gaseously sealing the axial lumen of the shaft.

17. An electrosurgical device comprising:
an elongate shaft having distal and proximal ends with an axial lumen therebetween;
interventional means at the distal end of the shaft;
means for mounting the interventional means to the shaft so as to reciprocate relative thereto;
a linkage slidably disposed in the axial lumen of the shaft and coupled to the interventional means;
a tubular housing generally aligned with the axial lumen having a distal end attached to the proximal end of the shaft, a proximal end opposite the distal end; and an axially-aligned elongate opening on a lateral side thereof;
a lever disposed in the elongate opening, the lever having a first end pivotally coupled to the housing and a second end opposite the first end; and
means in the housing for coupling the second end of the lever to the linkage, wherein the lever is pivotable relative to the housing between an outward position and an inward position to axially translate the linkage, thereby reciprocating the interventional means; and
means for locking the lever in the inward position, the means for locking comprising a thumb switch slidably disposed on the lever near the second end, a portion of the thumb switch being axially extendable from the second end, the housing having an internal aperture disposed adjacent the second end of the lever wherein the thumb switch may be extended into the aperture when the lever is in the inward position.

18. The electrosurgical device of claim 17 wherein the interventional means comprises a surgical hook fixed to the shaft and a paddle element coupled to the linkage so as to axially reciprocate relative to the hook.

19. The electrosurgical device of claim 17 wherein the interventional means comprises a fascia cutter; the fascia cutter comprising a transverse slot near the distal end of the shaft, and a blade mounted to the shaft so as to slide axially across the slot, the blade being coupled to the linkage so as to be axially reciprocated therewith.

20. The electrosurgical device of claim 17 wherein the interventional means comprises surgical scissors, the surgical scissors comprising a pair of blades pivotally coupled to the distal end of the shaft, the blades being coupled to the linkage so as to pivot about an axis perpendicular to the shaft when the linkage is translated.

21. The electrosurgical device of claim 17 further comprising means in the housing for locking the lever in the inward position.

22. The electrosurgical device of claim 17 wherein the linkage is electrically conductive the device further comprising means in the housing for connecting the linkage to an electrosurgical generator.

23. The electrosurgical device of claim 17 further comprising an aspiration port in the housing in communication with the axial lumen of the shaft.

24. An electrosurgical method comprising:
introducing an axial shaft of an electrosurgical device to an internal body location;
engaging a body structure with interventional means at a distal end of the shaft;
pivoting a lever axially aligned with and coupled to an axially-aligned tubular housing at a proximal end of the shaft about an axis perpendicular to the shaft from an outward position to an inward position to axially translate a linkage along the shaft, the linkage being coupled to the interventional means;
supplying electric current through the linkage to the interventional means to dissect and/or cauterize the body structure;
pivoting the lever, the interventional means comprising a surgical hook secured to the distal end of the shaft and a paddle element coupled to the linkage so as to reciprocate relative to the hook, such that the pivoting of the lever causes the paddle element to be axially translated adjacent to the hook; and
locking the lever in the inward position by sliding a thumb switch on the lever to engage the housing, the paddle element being in a distally extended position when the lever is in the inward position.

25. The method of claim 24 wherein the step of pivoting the lever further comprises the paddle element having a sharpened distal edge to assist in dissecting the body structure.

26. The method of claim 25 wherein the step of pivoting the lever further comprises configuring the distal edge of the paddle element to engage a proximally facing surface of the hook to assist in dissecting the body structure.

27. The method of claim 24 wherein the step of pivoting the lever further comprises the hook having at least one planar face and the paddle element including at least one planar surface configured to shear against the planar face of the hook to assist in dissecting the body structure.

28. The method of claim 24 further comprising delivering electrical energy to tissue through a lateral surface of the paddle element with the lever locked in the inward position.

29. The method of claim 24 wherein the body cavity is insufflated with a gas, the housing including means for gaseously sealing the axial lumen of the shaft.

30. The electrosurgical method of claim 24 further comprising the step of pivoting the lever, wherein the interventional means comprises a fascia cutter having an axially reciprocating blade movable across a transverse slot in the distal end of the shaft, such that the pivoting of the lever causes the blade to be translated across the slot to dissect tissue in the slot.

31. The electrosurgical method of claim 24 further comprising the step of engaging a body structure with the interventional means, wherein the interventional means comprises surgical scissors having a pair of blades which pivot about an axis perpendicular to the shaft in response to pivoting the lever.

* * * * *